(12) United States Patent
Lloyd

(10) Patent No.: US 6,623,526 B1
(45) Date of Patent: Sep. 23, 2003

(54) KNEE PROSTHESIS

(75) Inventor: Russell Lloyd, Swindon (GB)

(73) Assignee: Corin Limited, Gloucestershire (GB)

( * ) Notice: Subject to any disclaimer, the term of this patent is extended or adjusted under 35 U.S.C. 154(b) by 0 days.

(21) Appl. No.: 09/444,370

(22) Filed: Nov. 22, 1999

(30) Foreign Application Priority Data

Jan. 8, 1999 (GB) .............................................. 9900240

(51) Int. Cl.$^7$ ................................................. A61F 2/38
(52) U.S. Cl. .................................. 623/20.28; 623/20.29
(58) Field of Search .................. 623/20.28, 20.29–20.33

(56) References Cited

U.S. PATENT DOCUMENTS

| | | | | |
|---|---|---|---|---|
| 4,963,152 A | * | 10/1990 | Hofmann et al. | 623/20.14 |
| 5,201,881 A | * | 4/1993 | Evans | 623/20.14 |
| 5,344,460 A | * | 9/1994 | Turanyi et al. | 623/20.14 |
| 5,370,699 A | * | 12/1994 | Hood et al. | 623/20.14 |
| 5,609,639 A | * | 3/1997 | Walker | 623/20.14 |
| 5,879,394 A | * | 3/1999 | Ashby et al. | 623/20.14 |
| 5,928,286 A | | 7/1999 | Ashby et al. | |
| 6,068,658 A | * | 5/2000 | Insall et al. | 623/20.14 |

FOREIGN PATENT DOCUMENTS

| | | |
|---|---|---|
| FR | 2771281 A1 | 5/1999 |
| GB | 2304051 A | 3/1997 |
| GB | 2 304 051 | 3/1997 |
| GB | 2345446 A | 7/2000 |

* cited by examiner

*Primary Examiner*—David H. Willse
*Assistant Examiner*—Suzette J. Jackson
(74) *Attorney, Agent, or Firm*—Young & Thompson

(57) ABSTRACT

A knee prosthesis comprises, in combination, a tibial component, a femoral component and two meniscal components. One of the meniscal components is configured to co-operate with the tibial component such that relative movement therebetween is prevented. The other meniscal component is configured to co-operate with the tibial component such that limited relative movement therebetween is allowed. The tibial component has two fixed bollards projecting upwardly from an upper surface thereof. The two bollards have annular outwardly extending portions engageable in corresponding recesses in the one meniscal component in a snap fit manner.

9 Claims, 2 Drawing Sheets

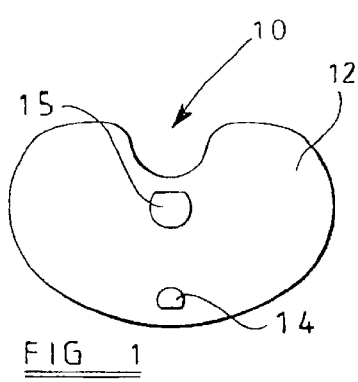
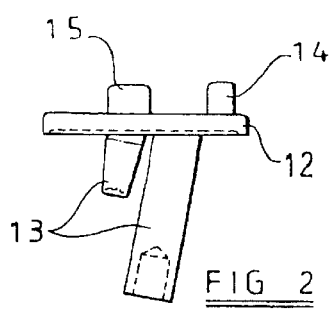
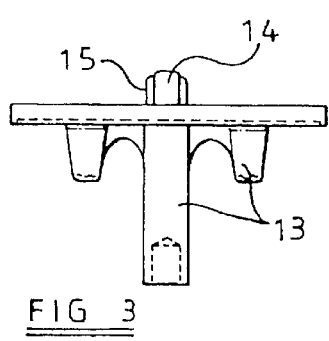
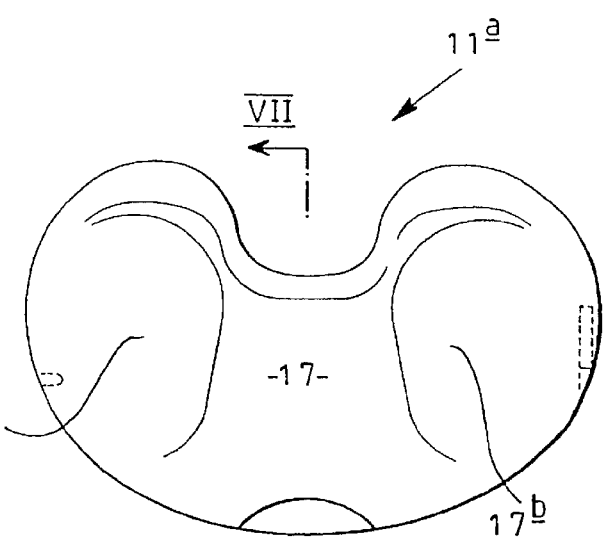
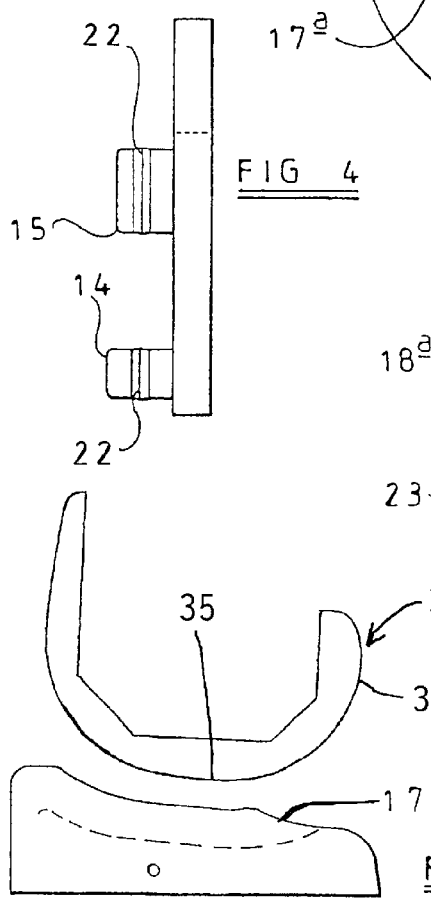

KNEE PROSTHESIS

The invention relates to a knee prosthesis.

Knee prostheses comprising a femoral component, a tibial component and a meniscal component are well known. Originally, all total knee prostheses had a fixed meniscal component. The concept of a mobile meniscal component is relatively new and is currently gaining considerable acceptance in the market. There is clear evidence that a mobile meniscus does have patient benefits. A mobile meniscus will be more appropriate for a patient with good knee ligamenture, rather than a patient who has a substantially osteo-arthritic deformed knee. There is, therefore, benefit n being able to choose between a fixed meniscus and a mobile meniscus inter-operatively and there is also benefit in having a knee system "on the shelf" which can be used in either form.

The selection of the prosthesis depends naturally, on the surgeon assessing the patient's requirements correctly. This can be difficult and the surgeon may, on occasion, be forced to make assumptions which eventually turn out to be incorrect. However, once a prosthesis has been implanted, it is extremely disruptive and inconvenient to remove it and replace it with a more appropriate prosthesis. For example, a surgeon may implant a prosthesis which allows limited relative movement between the tibial and meniscal components only to find at a later date that the patient does in fact require a prosthesis which allows no relative movement. In order to rectify the situation, the prosthesis may have to be removed completely and replaced.

GB-A-2304051 describes a knee prosthesis which allows the manner of operation of the knee to be varied to suit the patient's needs once the tibial and femoral components are in place by appropriate selection of the meniscal component. For example, one selectable meniscal component may be configured so as to be able to move in a limited manner in any one of the anterior-posterior, medial-lateral and rotational directions or in any combinations of these. Another meniscal component may be configured so as to engage with the tibial component such that no movement relative thereto is permitted. Thereby, the surgeon can select the manner of operation of the knee prosthesis from a number of possibilities without needing to select, order, obtain and check A-complete knee prosthesis.

A further advantage of this known prosthesis is that, should the implanted knee prove inadequate in its manner of operation, it is a relatively simple matter to replace the existing menisc component with an alternative which may perform better.

In this previously known prosthesis, the tibial component has two upstanding bollards which co-operate with recesses in the meniscal component. One of these bollards is slightly under-cut so that it can be brought into snap fitting engagement with a stepped recess in the meniscal component configured so as to engage with a tibial component such that no movement relative thereto is permitted. However, the other bollard is not under-cut and does not snap fit into the corresponding recess of the aforementioned meniscal component.

SUMMARY OF THE INVENTION

According to the present invention, there is provided a knee prosthesis comprising, in combination, a tibial component, a femoral component and two meniscal components, one of the meniscal components being configured to co-operate with the tibial component such that relative movement therebetween is prevented and the other meniscal component being configured to co-operate with the tibial component such that limited relative movement therebetween is allowed, the tibial component having two fixed bollards projecting upwardly from an upper surface thereof, the two bollards having annular outwardly extending portions engageable in corresponding recesses in the said one meniscal component in a snap-fit manner.

The fixed meniscal component of such a knee prosthesis has greater anti-destruction strength than is the case if only one bollard snap tits into a corresponding recess of the meniscal component.

Preferably, said other meniscal component has two recesses for receiving the two bollards, respectively, in such a way that limited relative movement between said other meniscal component and said tibial component is allowed, the walls of the recesses in said other meniscal component being provided with grooves to receive the annular outwardly projecting portions of the two bollards. The meniscal components are typically formed of ultra-high molecular weight polyethylene which tends to abrade to form polyethylene debris which may cause osteolysis and resultant failure of the knee prosthesis. The aforesaid grooves have the advantage that they prevent annular outwardly projecting portions of the two bollards from creating polyethylene debris. They also have the further advantage that they discourage vertical separation of the tibial and meniscal components.

Advantageously, one of the recesses of said one meniscal component has a ramp surface so as to allow its respective bollard to slide into place in said one recess. This allows the meniscal component to be glided into place between the tibial and femoral components during the course of an operation.

Preferably, the other recess of said one meniscal component is configured so that its respective bollard latches therein both horizontally and vertically.

The invention will now be more particularly described, by way of example, with reference to the accompanying drawings.

BRIEF DESCRIPTION OF THE DRAWINGS

FIG. 1 is a plan view of the tibial component of one embodiment of a knee prosthesis according to the invention, FIG. 2 is a side view of the tibial component shown in FIG. 1, FIG. 3 is a front view of the tibial component shown in FIG. 1, FIG. 4 shows the anterior and posterior bollards, respectively, of the tibial component shown in FIG. 1 on an enlarged scale, FIG. 5 is a plan view of a first meniscal component of a knee prosthesis according to the invention, FIG. 6 is a side view of the meniscal component shown in FIG. 5, FIG. 7 is a section taken along line VII—VII of FIG. 5.

DESCRIPTION OF THE PREFERRED EMBODIMENT

Figure 8:
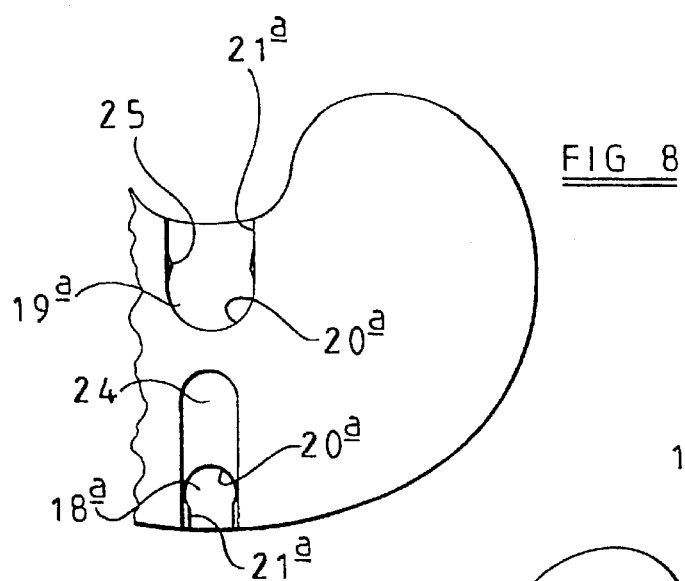
FIG. 8 is an underneath plan view of part of the meniscal component shown in FIG. 5.
Figure 9:
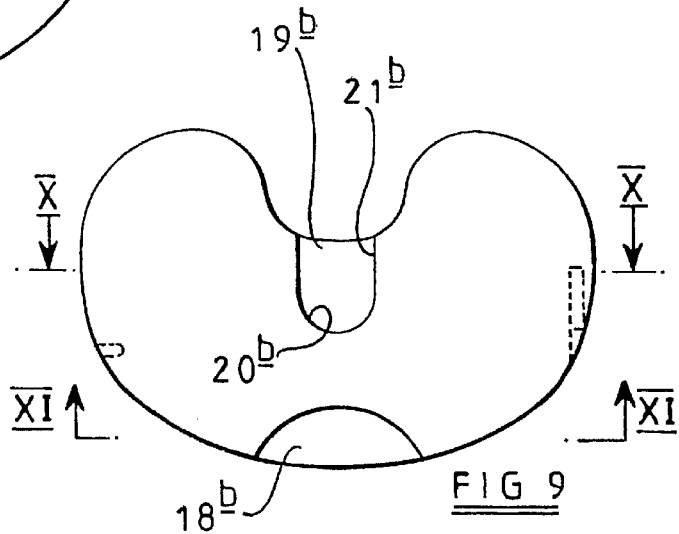
FIG. 9 is an underneath plan view of a second meniscal component of a knee prosthesis according to invention.

Referring now to the drawings, the prosthesis is a total knee prosthesis and consists of a conventional femoral component 30, a tibial component 10, and two alternative meniscal components 11a and 11b. The femoral component 30 is of standard design and shape, having fixing devices such as a femoral stem, or alternatively pegs or screws, and condyles 34. This component can be made of any biocompatible metallic material suitable for the purpose, but is preferably formed of cobalt chromium molybdenum alloy.

The tibial component 10 is also made of any biocompatible material suitable for the purpose but is also preferably made of high carbon cobalt chronium alloy.

The meniscal component 11a, is typically formed of ultra high molecular weight polyethylene.

The tibial component 10, shown in FIGS. 1 to 4, has a highly polished planar superior surface or plateau 12, beneath which are located fixing devices such as pegs or stems 13. An anterior bollard 14 and a posterior bollard 15 are located on the plateau 12. Each bollard 14, 15 is substantially cylindrical in shape and upstands from the plateau 12. The anterior bollard 14 is smaller in diameter than the posterior bollard 15.

Each meniscal component 11a, 11b has a generally planar inferior surface 16 and a superior surface 17 comprising two condylar surfaces 17a and 17b, one on either side of the center, each having a radius of curvature which is replicated in the articulating area 35 of the femoral component 30, as shown in FIG. 6.

The inferior surface 16 of the meniscal component 11a (shown in FIGS. 5 to 8) incorporates an anterior recess 18a and a posterior recess 19a. The two recesses 18a and 19a are generally U-shaped in underneath view and have an arcuate end wall 20a and substantially parallel side walls 21a. The distance between the side walls 21a of the posterior recess 19a is greater than the distance between the side walls 21a of the anterior recess 18a.

The bollards 14 and 15 fit snugly into the recesses 18a and 19a, respectively. Furthermore, the bollards 14 and 15 have annular outwardly extending portions 22, as shown in FIG. 4, which are engageable in grooves 23 in the recesses 18a and 19a in a snap-fit manner. As shown, the outwardly extending portions 22 of the bollards 14 and 15 are provided intermediate the top and bottom of each bollard. However, they could be at the top of one or each bollard 14, 15 in which case the corresponding groove or grooves 23 would be at the closed end of the respective recess or recesses.

The anterior recess 18a is provided with a ramp surface 24 which is inclined away from the inferior surface 16 of the meniscal component 11a in a direction away from the posterior recess 19a and towards the anterior recess 18a. This ramp surface 24 allows the anterior bollard 14 to slide into place in the anterior recess 18a. The meniscal component 11a can thus be glided into place between the tibial and femoral components during the course of an operation.

The posterior recess 19a has two opposed inwardly directed protrusions 25 which latch the posterior bollard 15 horizontally. This bollard 15 is latched vertically by virtue of the fact that the outwardly projecting portion 22 of the bollard 15 snap fittably engages in the groove 23 of the posterior recess 19.

The inferior surface 16 of the other meniscal component 11b also incorporates an anterior recess 18b and a posterior recess 19b. The anterior recess 18b is substantially part-circular in underneath view, having a part-cylindrical inner wall and a relatively wide opening in the side wall. The posterior recess 19b is generally U-shaped in underneath view, having an arcuate end wall 20b and substantially parallel side walls 21b. The distance between the parallel side walls 21b of the posterior recess 19b is less than the overall width of the anterior recess 18b.

The fact that the anterior recess 18b is wider than the posterior recess; 19b, and also that the anterior bollard 14 is smaller in diameter than the posterior bollard 15, means that, when the posterior bollard 15 abuts against a side wall 21b of the posterior recess 19b at an extreme of medial-lateral movement, rotational movement of the meniscal component 11b with respect to the tibial component 10 about an axis passing through or close to the posterior bollard is still possible. This is advantageous in helping to mimic very closely the action of a natural knee joint.

Figure 10:
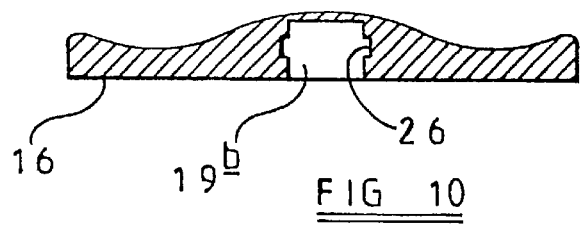
FIG. 10 is a section taken along line X—X of FIG. 9.
Figure 11:
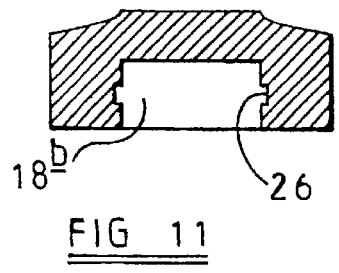
FIG. 11 is a section taken along the line XI—XI of FIG. 9.

As shown in FIGS. 10 and 11, the anterior and posterior recesses 18b and 19b, respectively, are provided with grooves 26 which will loosely receive the outwardly projecting portions 22 of the bollards 14 and 15 and will thus prevent these projecting portions from creating polyethylene debris by rubbing against the walls of the recesses 18b and 19b. They also have the advantage that they discourage vertical separation of the tibial and meniscal components 10 and 11b, respectively.

Bone-contacting surfaces of the femoral and tibial components may have appropriately textured areas or porous coatings of material such as Hydroxyapatite.

Although metal is presently preferred as the material for the femoral and tibial components, it is envisaged that they could be made of (or coated with) a ceramic material (e.g. alumina or zirconia) or glass or coated with diamond or a diamond-like material.

What is claimed is:

1. A knee prosthesis comprising, in combination, a tibial component, a femoral component and two meniscal components, one of the meniscal components being configured to co-operate with the tibial component such that relative movement therebetween is prevented and the other meniscal component being configured to cooperate with the tibial component such that limited relative movement therebetween is allowed, the tibial component having two fixed bollards projecting upwardly from an upper surface thereof, the two bollards having annular outwardly extending portions engageable in corresponding recesses in said one meniscal component in a snap-fit manner.

2. A knee prosthesis as claimed in claim 1, wherein said other meniscal component has two recesses for receiving the two bollards, respectively, in such a way that limited relative movement between said other meniscal component and said tibial component is allowed, the walls of the recesses in said other meniscal component being provided with grooves to receive the annular outwardly projecting portions of the two bollards.

3. A knee prosthesis as claimed in claim 1, wherein one of the recesses of said one meniscal component has a ramp surface so as to allow its respective bollard to slide into place in said one recess.

4. A knee prosthesis as claimed in claim 3, wherein the other recess of said one meniscal component is configured so that its respective bollard latches therein both horizontally and vertically.

5. A knee prosthesis as claimed in claim 1, wherein said other meniscal component is capable of anterior-posterior and/or medial-lateral and rotational movement relative to the tibial component.

6. A knee prosthesis as claimed in claim 1, wherein the femoral and tibial components are made in any biocompatible metallic material suitable for the purpose.

7. A knee prosthesis as claimed in claim 6, wherein the femoral and tibial components are made of cobalt chromium molybdenum alloy.

8. A knee prosthesis comprising:

a tibial component comprising a first and a second projection extending from a first surface, said first and said second projections each having an outwardly extending generally annular portion with one flat side;

a meniscal component having a first surface including a first and a second recess arranged and adapted for detachably engaging said first and said second portions, respectively, in a snap-fit engagement to prevent relative movement between said tibial component and said meniscal component; and a femoral component having an articulated area arranged and adapted for receiving a second surface of said meniscal component.

9. A knee prosthesis comprising:

a tibial component comprising two projections on a first surface thereof, said two projections each having a generally annular shaped outwardly extending portion with one flat side;

a meniscal component comprising a first surface having two recesses for receiving said two projections and for allowing limited relative movement between said meniscal component and said tibial component; and a femoral component having an articulated area arranged and adapted for receiving a second surface of said meniscal component, said recesses having grooved walls for receiving said outwardly extending portions.

\* \* \* \* \*